(12) United States Patent
Catani et al.

(10) Patent No.: US 10,092,026 B2
(45) Date of Patent: *Oct. 9, 2018

(54) ENHANCED NATURAL SWEETENER AND METHOD OF MAKING

(75) Inventors: Steven J. Catani, Athens, GA (US); Juan L. Navia, Doylestown, PA (US)

(73) Assignee: Heartland Consumer Products LLC, Carmel, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/367,630

(22) Filed: Feb. 7, 2012

(65) Prior Publication Data

US 2012/0201952 A1    Aug. 9, 2012

Related U.S. Application Data

(60) Provisional application No. 61/440,512, filed on Feb. 8, 2011.

(51) Int. Cl.
| | | |
|---|---|---|
| A23L 27/30 | (2016.01) | |
| A23L 5/00 | (2016.01) | |
| C07H 1/08 | (2006.01) | |
| C07H 15/24 | (2006.01) | |
| A23L 29/30 | (2016.01) | |

(52) U.S. Cl.
CPC ............... *A23L 27/36* (2016.08); *A23L 5/00* (2016.08); *A23L 27/30* (2016.08); *A23L 29/30* (2016.08); *C07H 1/08* (2013.01); *C07H 15/24* (2013.01)

(58) Field of Classification Search
CPC ........ A23L 1/221; A23L 1/236; A23L 1/2366; A23L 27/36
USPC ........................................................ 426/548
See application file for complete search history.

(56) References Cited

U.S. PATENT DOCUMENTS

| | | | | |
|---|---|---|---|---|
| 2,559,129 | A * | 7/1951 | Miller | .............................. 95/245 |
| 3,503,854 | A * | 3/1970 | Good | ....................... C11B 1/108 |
| | | | | 202/154 |
| 4,113,573 | A * | 9/1978 | Gerow | ............................... 203/2 |
| 4,282,264 | A * | 8/1981 | Magnolato | ..................... 426/599 |
| 4,590,160 | A * | 5/1986 | Nishihashi et al. | ............. 435/78 |
| 5,972,120 | A * | 10/1999 | Kutowy et al. | .................. 127/43 |
| 6,149,957 | A * | 11/2000 | Mandralis et al. | ............ 426/387 |
| 8,299,224 | B2 * | 10/2012 | Abelyan | ................ C07H 15/24 |
| | | | | 536/128 |
| 2006/0003053 | A1 | 1/2006 | Ekanayake | |
| 2006/0068073 | A1* | 3/2006 | Catani et al. | .................. 426/548 |
| 2006/0083838 | A1* | 4/2006 | Jackson et al. | ................ 426/548 |
| 2006/0142555 | A1 | 6/2006 | Jonnala | |
| 2007/0231414 | A1* | 10/2007 | Aoki et al. | ..................... 424/725 |
| 2008/0292764 | A1 | 11/2008 | Prakash | |

(Continued)

FOREIGN PATENT DOCUMENTS

JP    56-026168    *    3/1981    ............... A23L 1/22

OTHER PUBLICATIONS

PCT Search Report for PCT/US2012/024157 dated Apr. 13, 2012.

(Continued)

*Primary Examiner* — Jeffrey Mornhinweg

(57) ABSTRACT

A natural sweetening composition comprising a crude mixture of at least one plant based natural high intensity sweetening compound, the sweetening composition made by the process comprising (a) the step of steam stripping the crude mixture; and (b) at least one step of filtering the crude mixture.

17 Claims, 2 Drawing Sheets

(56) References Cited

U.S. PATENT DOCUMENTS

2008/0300402 A1* 12/2008 Yang ..................... A23L 1/3002
536/128
2009/0017185 A1* 1/2009 Catani .......................... 426/658

OTHER PUBLICATIONS

PCT Search Report for PCT/US2012/024159 dated Apr. 16, 2012.
Martelli A. et al., "Unusual essential oils with aromatic properties. I. Volatile components of Stevia rebaudiana Bertoni." Flavour and Fragrance Journal vol. 1, No. 1, Nov. 1985 (Nov. 1985), pp. 3-7, XP002671983, DOI:10.1002/FFJ.2730010103 p. 3-p. 4.

* cited by examiner

ENHANCED NATURAL SWEETENER AND METHOD OF MAKING

CROSS-REFERENCE TO RELATED APPLICATION

The present application claims the benefit of priority to U.S. Provisional Application Ser. No. 61/440,512, filed Feb. 8, 2011, the contents of which are completely incorporated by reference.

BACKGROUND OF THE INVENTION

Field of the Invention

The present invention relates to sweetening compositions. More particularly, the present invention relates to a natural sweetener that has enhanced flavor attributes and the method of making the natural sweetener.

The market for natural foods is growing rapidly as more and more consumers are making a conscious choice to purchase food products that are natural. To protect and assist consumers, governmental agencies such as the Canadian Food Inspection Agency, have proposed standards to assure the natural status of various food ingredients.

This trend is also evident in the sweetener category, where natural sweetener products are gaining in popularity. Many consumers are looking for natural sweeteners that provide the sweet taste they want with less calories than sugar.

Even so, some low or high intensity sweeteners are produced using chemical treatments (addition of calcium carbonate, alumina or other clarifying chemicals), or treatments with ion exchange resins, or crystallization from non-food grade solvents. These commonly used methods fail to satisfy the regulatory guidelines for how a natural tasting sweetener is made in many countries.

Moreover, many have tried using various methods to formulate a table top sweetener using natural ingredients. Often the formulation of the product has been adjusted to try to hide or overcome the undesirable taste perceptions inherent in the natural sweetener product. In many instances, the resulting product no longer has a natural taste. Rather, consumers find some of these products have an artificial candy like flavor. And in some instances, the undesirable taste and flavor notes, which consumers do not like are still present.

Clearly, consumers want a natural sweetener product that has a natural taste without an artificial taste and/or bitter taste.

BRIEF SUMMARY OF THE INVENTION

The present invention is directed to a natural sweetening composition comprising a crude mixture of at least one plant based natural high intensity sweetening compound, the sweetening composition made by the process comprising (a) the step of steam stripping the crude mixture; and (b) at least one step of filtering the crude mixture.

DETAILED DESCRIPTION OF THE INVENTION

Figure 1:
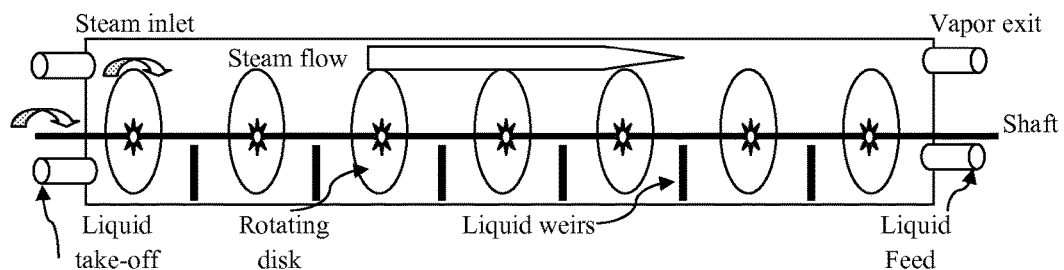
FIG. 1 depicts a typical Steam Stripper schematic.

As used herein, a gram of Sucrose Equivalent Sweetness ("SES") is understood to mean the amount of low or high intensity sweetener needed to be added to an 8 ounce glass of water in order to provide the same sweetness as an independent 8 ounce glass of water containing one gram of sucrose. For example, about $\frac{1}{250}$ g of rebaudioside A will equal about one gram of SES because rebaudioside A is about 250 times sweeter than sucrose. Similarly, about $\frac{1}{50}$ g of glycyrrhizin will provide one gram of SES because glycyrrhizin is about 50 times sweeter than sucrose.

As used herein, a low intensity sweetener delivers between 0.5 to 2 grams of sucrose-equivalent sweetness (SES) per gram of solids. Other plant-derived low-intensity sweeteners include erythritol, xylitol, maltitol, maltooligosaccharide, mannitol, sorbitol, tagatose, glucose, fructose and sucrose. Since some of these are less sweet than others, the proportions and concentration of these sweeteners will affect the sweetness quality of the composite.

As used herein a "high intensity sweetener" delivers 50 grams of SES or more per gram of solids. As disclosed herein a high intensity plant based sweetener could be the extract or concentrate of the Monk fruit, also known as Luo Han Guo, or Stevia rebaudiana.

As used herein, "plant based" is understood to mean a compound or combination of compounds naturally providing the principle sweetness in a plant. Further, it is understood to include sweeteners modified by enzymatic or microbial means resulting in a compound or combination of compounds naturally providing the principle sweetness in a plant.

The present inventors have devised a method of making a natural sweetening composition, which produces a natural tasting sweetener product. The natural sweetening composition includes an extract or crude mixture of at least one plant based natural high intensity sweetening compound, or the combination of at least one plant based natural low intensity sweetening compound and at least one plant based natural high intensity sweetening compound. These components along with the remaining components of the composition form the extract or crude mixture, which is treated by (a) steam stripping, and (b) treating the extract or crude mixture to at least one step of filtering (clarification and/or extraction).

The crude plant extract is processed through a steam stripping column, thereby producing a steam stripped extract. The steam stripped extract is then filtered. For example, the extract mixture is pumped into the top portion of a packed or tray column tower, where the mixture comes in intimate contact with steam that enters through the bottom portion of the tower. As a result of the contact between the mixture and the steam, volatile components from the extract mixture are transferred to the vapor phase, thus purifying the extract mixture.

Conditions and Parameters for Combine Use of Steam-Striping and Filtration:

Steam-to-feed ratio. The proportions of steam (for example, as kg of water vapor unit volume of feed per unit time) to the feed rate can be varied depending on the efficiency of the column and the extent to which volatile components need to be removed.

Temperature of the feed and the steam at the point of entry into the column. Pre-heating the feed and or super-heating the steam can prevent some degree of condensation and improve the efficiency of the operation in removing volatiles. As such, the heat balance must be maintained so that enough liquid remains to keep the desirable non-volatile components in the liquid phase and moving down the steam stripping column.

Column and packing material geometry. The proportions of the column (height relative to circumference) and the shape of the packing material should be such that it minimizes the amount of "channeling" of either vapor moving up, or liquid moving down, such that the two phases fail to make necessary contact. Optimally, liquid and vapor will be in close contact throughout the column so that the column operates at close to the predicted number of theoretical plates. Similarly, the column will be operated in a vertical position and the packing or redistributor plates selected offer minimal or no liquid hold-up.

The ratio of product output to the feed rate will be optimally close to 1.0, but the column may be operated optionally to increase the product take-off rate at the bottom relative to feed rate. A more dilute product will result, or take a smaller bottoms rate (net greater evaporation of the feed stream resulting in more concentrated bottoms) relative to feed rate.

In either case, the sum of:

Liquid feed+steam feed=bottoms+vapor tops will hold true otherwise the column will be accumulating an inventory of liquid and will quickly flood.

The point of entry of liquid and vapor feed, and take-off of product can vary depending on the column design and the efficiency of operation. Although the Examples which follow depict/discuss an apical feed and bottom take-off, the feed can be introduced axially along the column at one or more points. Moreover, product and/or steam may be introduced at one or several points along the sides of the column. The conditions of operation of this column are inherent in the design and can be selected to yield a specific product composition with respect to the volatile components and concentration of non-volatiles.

Ideally, steam quality should be compatible with food. However, some steam generators use chemicals or other additives (to protect the boiler) that may be volatile and that may be carried into the product in the bottoms (or the steam/vapor at the top, if that is the desired product stream). Thus, it is preferable to avoid the use of boiler chemicals in order to generate clean steam for the process.

In one embodiment, the process of steam stripping is carried out such that contact between vapor (steam) and liquid is intimate and rapid. For example, this may be accomplished by conducting the process in a configuration that enables the flow of steam in a direction opposite (counter-current) to the flow of the liquid feed. Steam stripping may be accomplished vertically with counter-current flows of liquid (down) and vapor (up).

Alternatively, steam stripping may be accomplished in a hybrid manner as shown in FIG. 1. In FIG. 1, the liquid is brought into the vapor phase by mechanical means (such as a rotation disk or by spraying) while the liquid flows by passive overflow of the weirs (e.g., if the vessel is inclined slightly where feed is higher than the take-off point) or pumped from one chamber to the next.

Depending on the conditions of operation, this is considered to be steam stripping because in fact the liquid is moving counter-current to the flow of the steam.

Another critical step in the method is the step of filtration (clarification and/or fractionation), where filtration is used to purify a liquid, i.e., extract the mixture by separating particles from the liquid. Basically, solvent is passed through a semi-permeable barrier. The size of the pores in the barrier determines the barrier's permeability, allowing solvent and particles smaller than the size of the pores to pass through the barrier, while retaining or rejecting particles which are larger than the pores. This provides a way to separate undesirable components from the liquid solvent, resulting in a purified liquid that is clean and filtered on one side of the barrier, with the removed solute particles on the other side. In a preferred embodiment, membrane filtration may be used to remove fine particulate matter, color particles, and macromolecules such as proteins and polysaccharides. Membrane filtration can be used to enrich some components while depleting or removing others. This recognizes that the separation based on size does not need to be complete to be effective and useful. In another embodiment, other stationary media that can be employed for filtration, such as separations based on solute or particle size using resin beads, or molecular sieve particles made from clays or ceramics, and other similar materials and the like.

The filtration step may be employed prior to, after, or prior to and after the steam stripping step.

Membrane Fractionation Parameters:

One form of filtration is molecular filtration, which is accomplished with semi-permeable membranes (membrane fractionation) filtration. This basically involves partitioning solutes across a semi-permeable membrane on the basis of their molecular size. The empirical equation generally used to predict or model the behavior of solutes is:

% Rejection=(log($C_r/C_o$))/(log($V_o/V_r$))×100%

Where:

$C_r$=concentration of given solute in the retentate $C_o$=concentration of given solute in the original (feed) solution $V_o$=initial volume of feed $V_r$=volume of the retentate Retentate=that portion of the feed solution that does not go through the membrane Permeate=the portion of the feed solution that passes through the membrane All membrane fractionations assume some moderate temperature control since temperature can affect the permeability of the membrane, and therefore the apparent % rejection (% R) of a solute. It should be understood that the temperature of the product will be dependent upon the desired results and can be determined empirically during processing/operation. In one embodiment, the temperature of the product is in the range of from about 15 to about 100° C.

The molecular size of the solute has more to do with shape and volume, and electronic charge of the solute than its molecular weight (MW), but MW can be a useful way to distinguish which solutes are likely, or not, to pass through a membrane.

The size and shape of the complex molecules in a plant extract can be affected by other solutes, including some that may be removed during steam stripping.

Figure 2:
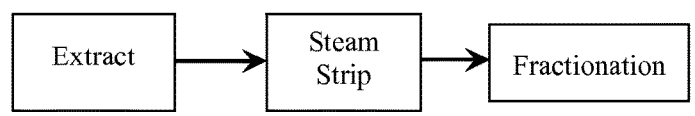
FIG. 2 depicts a process flow diagram where an extract is processed according to one embodiment of the invention.
Figure 3:
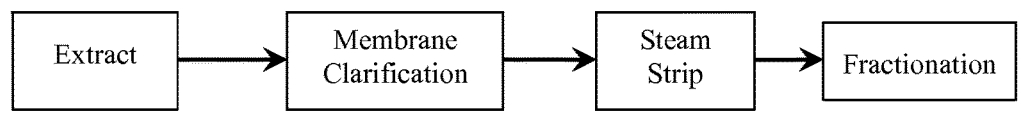
FIG. 3 depicts a process flow diagram where an extract is processed according to another embodiment of the invention.
Figure 4:
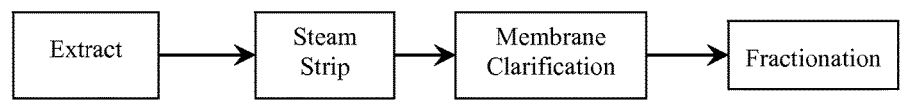
FIG. 4 depicts a process flow diagram where an extract is processed according to yet another embodiment of the invention.
Figure 5:
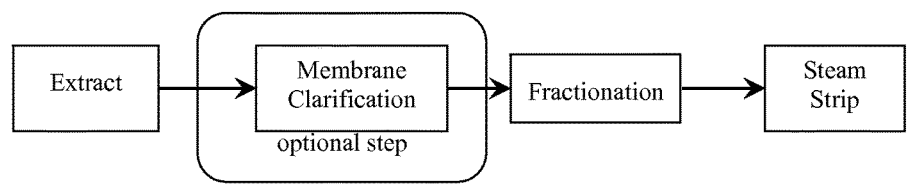
FIG. 5 depicts a process flow diagram where an extract is processed according to still yet another embodiment of the invention.
Figure 6:
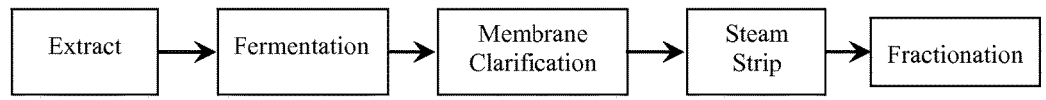
FIG. 6 depicts a process flow diagram where a fermentor product is processed according to an embodiment of the invention.

Several embodiments of the inventive process utilizing steam stripping with filtration are depicted in FIGS. 2-6. The process alternatives shown in FIGS. 2-6 illustrate a variety of combinations of steam-stripping with filtration processing (clarification and fractionation). FIG. 2 depicts a process flow schematic where an extract is treated to steam stripping and fractionation. In FIG. 3, a process flow schematic is shown where an extract is treated to membrane clarification, steam stripping and fractionation. In FIG. 4, a process flow schematic is shown where an extract is treated to steam stripping, membrane clarification and fractionation. FIG. 5 depicts a process flow schematic where an extract is treated to fractionation and steam stripping, where the extract may optionally be treated to the step of membrane clarification prior to fractionation. And in FIG. 6 a process flow schematic is shown where an extract is treated to fermentation (enzyme modification) to form a fermentor product which is treated to membrane clarification, steam stripping and fractionation. It should be understood that FIG. 6 exemplifies one particular embodiment, however, the fermentation (enzyme modification) step may occur after (i) membrane clarification, (ii) steam stripping, or (iii) fractionation. That is, the sequential position of the fermentation (enzymatic modification) step in addition to the subsequent processing steps may be varied. All combinations are intended as part of the invention.

Clarification here is a form of filtration to remove very small particles down to the size of bacterial cells or spores, or possibly some viruses. In contrast, fractionation is more at the level of macromolecules or smaller, down to a water molecule. A semi-permeable membrane used to effect clarification or fractionation can be characterized in terms of its porosity. The term nominal molecular weight cut-off (nm-wco) is used by those skilled in the art to describe the porosity of the membrane in terms of the approximate upper limit of size molecule that the semi-permeable membrane will allow to pass (or lower limit of retention). This is understood to be a descriptive term since the effective porosity can vary with the operating temperature, the system pressure and the geometry of the solute particles, among other factors. The specific selection of a membrane is highly empirical and is typically the result of experimentation. It is understood that clarification and filtration materials may be laminated products, porous metals, or non-metals such as ceramics, glass, carbon, and other materials.

Optionally, the process may include a drying step. Any suitable means of drying the natural sweetening composition may be employed.

The improved natural flavor quality may be perceived as a more pleasant sweet taste with less "green" notes characteristic of crude plant extracts, reduced off-flavors from undesirable extractable components (possibly from surface components), or reduced bitter notes in the extract.

Plant based natural low intensity sweeteners include, but are not limited to, fruit-derived sweeteners such as D-fructose, also known as levulose D-arabino-2-hexulose, or "Fruit Sugar" which is found in many fruits. Other examples are concentrated or dried fruit juices, such as the juices from apples, grapes, or the like.

Plant based natural high intensity sweeteners include, but are not limited to, plant matter from *Stevia rebaudiana* Bertoni, plant matter from liquorice root *Glycyrrhiza glabra* and/or plant matter from the fruit of a herbaceous perennial vine native to southern China, *Siraitia grosvenorii*, known by the botanical synonyms *Momordica grosvenorii* and *Thladiantha grosvenorii*, Monk fruit (commonly referred to as Luo Han Guo).

Additionally, a variety of ingredients may be included in the sweetening composition of the present invention.

For example, a bulking agent or other carrier material may be included. Among those disclosed or used include fructooligosaccharide (FOS) and other fibers, maltooligosaccharides, and erythritol. Erythritol is especially popular as it can mitigate some of the bitter taste. The carrier material may be in the form of a simple mixture, or co-crystallized with the high intensity sweetener.

Other fruit extracts may contribute additional flavor or color attributes that can elicit the perception of "natural" in the sweetener. Strawberry or blueberry flavored syrups or other berry syrup solids, as well as various concentrated fruit juices comprise a number of sweet and non-sweet compounds that contribute to the perception of "natural."

Often the makers or users of these sweeteners add other components to them to overcome a less pleasant taste, e.g., a bitter taste.

Another optional ingredient in the composition of the present invention is a soluble food ingredient. The soluble food ingredient may be, for example, a fructooligosaccharide (FOS), a digestion resistant maltodextrin (e.g., Fiber-Sol), erythritol, inulin, a sugar polymer, or any combination thereof. Preferably, the soluble food ingredient is a fiber.

Vitamins and minerals may also be present.

The compositions may contain other components, including flavor, aroma, other nutritional components, binders, and mixtures thereof.

The tabletop sweeteners disclosed, can be amorphous or crystalline solids, liquids, or syrups. They can be produced by any number of processes known to those skilled in the art.

Preferably the tabletop sweetener compositions have less than 2.5 kcals per teaspoon (equal in sweetness to 1 tsp of sucrose), but can be formulated to deliver a wide variety of caloric contents less than the 4 kcals per gram of SES (the caloric value of sucrose). For example, the compositions can be formulated using techniques known to those working in the area, such as low bulk density spray drying, to any practical density.

The natural sweetener composition has less than 2 kcal per gram of SES. In one embodiment, the sweetening composition has less than 1 kcal per gram of SES. In another embodiment, the sweetening composition has less than 0.5 kcal per gram of SES. In yet another embodiment, the sweetening composition has less than 0.25 kcal per gram of SES.

Additionally, the natural sweetener composition has a density of from about 0.1 g/cm$^3$ to about 0.8 g/cm$^3$.

The natural sweetener composition has a ratio of carrier material to plant based natural high intensity sweetening compound of from about 1:1 to about 99:1. In one embodiment, the ratio of carrier material to plant based natural high intensity sweetening compound of from about 10:1 to about 90:1. In another embodiment, the ratio of carrier material to plant based natural high intensity sweetening compound of from about 25:1 to about 50:1. In yet another embodiment, the ratio of carrier material to plant based natural high intensity sweetening compound of from about 30:1 to about 40:1.

The tabletop sweeteners compositions can be delivered in any format known to those skilled in the art. For example, sachets, bulk bags, etc.

Unless otherwise defined, all technical and scientific terms used herein have the same meaning as commonly understood by one of ordinary skill in the art to which this invention pertains. The materials, methods, and examples described herein are illustrative only and not intended to be limiting.

The following example is provided to further illustrate the compositions and methods of the present invention. The example is illustrative only and is not intended to limit the scope of the invention in any way.

Example 1

Combined Steam Strip and Membrane Filtration

Extraction:

Dried, coarsely chopped leaves of *Stevia rebaudiana* (Bertoni) (0.8 kg) were immersed in city water (5.85 kg) inside a Groen (Model: TDB/7-23) kettle and the mixture was brought to a boil. The mixture was kept at a slow simmer for several minutes, then allowed to cool for a few hours, until it was just warm to the touch. The aqueous liquor was decanted away from the leaf mass, and the leaves pressed by hand to remove as much of the extract as possible. The leaf mass was discarded and the extract (3.8 kg, less samples) was carried on to the steam stripping stage. The extract was very dark in color and very turbid, even after filtration through a 200 mesh screen.

Steam Stripping:

The steam stripper was operated as a single stage, but additional stages could have been inserted. There were three sections: (1) the head cap, with a feed inlet centered over the barrel and a tops vapor outlet than could have been connected to a condenser; (2) the barrel, which holds the packing material and hold-downs; and (3) the bottoms take-off, which also had a steam inlet positioned off-center to prevent liquid tricking down the column from blocking steam entering the column barrel. The exterior of the column was insulated to minimize heat loss and condensation on the walls of the barrel.

The extract was fed at the top of the column at about 5 mL/min against an established steam flow of about 96 mL/min (measured as condensate). Steam stripper bottoms were collected semi-continuously by adjusting the aperture of the stopcock of the bottoms take-off. Approximately 6.7 kg of steam stripped bottoms were collected over about 75 minutes (89 mL/min; about 39 mL/min of condensate from steam). The combined steam stripper bottoms were sampled and the rest was used for the membrane clarification stage. Steam stripper bottoms were observed to be as black as the steam stripper feed, but completely free of the grassy, herbal odor notes prominent in the crude extract, and characteristic of boiled Stevia leaves.

Membrane Clarification:

Clarification was accomplished using a KOCH membrane test unit (KPN 0210090) fitted with a 1" hollow fiber test cartridge (PM2) of about 2000 nm wco. The steam stripper bottoms was recirculated for a few minutes without back pressure to establish flow, then backpressure was applied by gradually tightening a pinch clamp on the membrane discharge side until a slow permeate flow was achieved (about 4 mL/min). This continued until 1.25 kg of permeate was collected. Samples of permeate and retentate were collected as retained samples. The permeate appeared completely transparent and had a slight golden color. Both permeate and retentate exhibited a strong sweet taste characteristic of steviol glycosides, but the permeate had a less pronounced bitter aftertaste.

Since the fractionation process is non-destructive, composition of the feed (Co) can be calculated by adding back the components from permeate and retentate as shown:

$$Co=[(Cp \times Mp)+(Cr \times Mr)]/Mo \times 100\%$$

Where:

Cp=concentration of given solute in the permeate

Mp=mass of the permeate

Table 1 below shows the % rejection calculated for some representative steviol glycosides. The identity of the steviol glycosides was established by relative HPLC mobility relative to known standards and confirmed by mass spectrometry.

TABLE 1

| | | Reb F | Reb A (& Stevioside) | Reb D | Reb C | Dulcoside A | Mass (kg) |
|---|---|---|---|---|---|---|---|
| Formula weight | | 936 | 966 (804) | 1128 | 950 | 788 | |
| Calculated | Co | 5.1% | 29.4% | 2.6% | 6.9% | 1.9% | 5.7 |
| % Peak area | Cr | 5.66% | 30.27% | 2.87% | 7.57% | 2.00% | 4.5 |
| % Peak area | Cp | 3.01% | 25.30% | 1.50% | 4.32% | 1.67% | 1.25 |
| Calculated | % Rejection | 41.71% | 11.68% | 42.65% | 37.75% | 11.76% | |

The observed % rejection can be influenced by the concentration in the feed as well as the molecular size. These results are understood to mean that all the components are permeable to the membrane, whereas the color bodies and some bitter components are much less so. The results demonstrate how membrane fractionation, in conjunction with steam-stripping, may produce a cleaner, more desirable steviol glycoside stream without the need for resin treatment or crystallization from organic solvents such as methanol or ethanol.

Example 2

Extraction:

Dried, coarsely chopped leaves of *Stevia rebaudiana* (Bertonii) (1 kg) were immersed in city water (8.5 kg) inside a Groen (Model: TDB/7-23) kettle and the mixture brought to a boil. The mixture was kept at a slow simmer for several minutes, and allowed to cool for a few hours until it was just warm to the touch. The aqueous liquor was decanted away from the leaf mass, and the leaves pressed by hand to remove as much of the extract as possible. The leaf mass was discarded and the extract (5.4 kg, less samples) was carried on to the steam-stripping stage. The extract was very dark in color, and very turbid, even after filtration through a 200 mesh screen.

Steam Stripping:

The steam-stripper (SS) was operated in a 2-stage mode. Extract was fed (about 12 mL/min.) at the top of the column against an established steam flow of about 150 mL/min (measured as condensate). Steam stripper bottoms were collected semi-continuously by adjusting the aperture of the stopcock of the bottoms take-off. Approximately 7.85 kg of steam-stripped bottoms were collected over about 195 minutes (range 45 to 91 mL/min.). The combined steam-stripper bottoms were sampled and the rest was used for the membrane clarification stage. Steam-stripper bottoms were observed to be as black as the steam-stripper feed, but completely free of the grassy, herbal odor notes prominent in the crude extract, and characteristic of boiled Stevia leaves.

2-Stage Membrane Fractionation

Stage 1: Fractionation was accomplished using a KOCH membrane test unit (KPN 0210090) fitted with a 1" hollow fiber test cartridge (PM10) of about 10,000 nm wco. The steam-stripper bottoms (7.8 kg) was recirculated for a few minutes without back pressure to establish flow, then backpressure applied by gradually tightening a pinch clamp on the membrane discharge side until 80 mL/min permeate flow was achieved. This continued until 5.65 kg of permeate was collected (2 hours). Samples of permeate, and retentate (2 kg) were collected as retained samples. The permeate appeared very dark in color, but devoid of particulate matter. The permeate and retentate exhibited a strong sweet taste characteristic of steviol glycosides.

Stage 2: The second membrane fractionation was accomplished with a 1" hollow fiber test cartridge (PM2) of about 2,000 nm wco. The First Stage Permeate (5.65 kg) was recirculated for a few minutes without back pressure to establish flow, then backpressure applied by gradually tightening a pinch clamp on the membrane discharge side until 5.5 mL/min permeate flow was achieved, which increased gradually to 17 mL/min as the feed warmed from 19° C. to 38° C. 2.05 kg of permeate was collected (3.5 hours). Samples of permeate, and retentate (3.65 kg) were collected for analysis. Permeate appeared a light golden color. Permeate and retentate exhibited a strong sweet taste characteristic of steviol glycosides.

Estimation of % Rejection

Table 2 below shows the % rejection calculated for some representative steviol glycosides. The identity of the steviol glycosides was established by relative HPLC mobility relative to known standards and confirmed by mass spectrometry.

The results demonstrate how membrane fractionation, in conjunction with steam-stripping, may produce a cleaner, more desirable steviol glycoside stream without the need for resin treatment or crystallization from organic solvents such as methanol or ethanol.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A natural sweetening composition comprising naturally occurring high intensity sweetener components having improved natural flavor qualities, wherein said natural sweetening composition is made by a process consisting of:
   (a) preparing a crude plant extract from natural high intensity sweetening compound selected from the group consisting of steviol glycosides, glycyrrhizin, mogrosides, and mixtures thereof by boiling dried, coarsely chopped leaves in water to form an aqueous liquor and plant mass, decanting the aqueous liquor away from the plant mass,
   (b) providing at least one step of steam stripping the crude extract through a steam stripping column, wherein the steam stripping column has a head cap with a feed inlet and a vapor outlet disposed on a first end of the column and a bottom take-off with steam inlet and feed outlet disposed on an opposing second end of the column, and establishing a countercurrent flow by:
       (i) allowing the crude extract to flow from the first end of the column against a rate of steam that flows from the opposing second end,
       (ii) establishing the steam flow at a feed ratio of about 12:1 to about 19:1 relative to the extract feed rate,
       (iii) transferring the volatile components to a vapor phase,
       (iv) removing from the crude extract the volatile components;

TABLE 2

| | | Reb F | Reb A & Stev | Reb D | Reb C | Dulc A | Mass (kg) |
|---|---|---|---|---|---|---|---|
| | | PM10 Membrane #1 Product Steam stripper bottoms | | | | | |
| Peak Area | Feed | 4.3% | 23.7% | 4.8% | 6.8% | 2.2% | 7.85 |
| Peak area | Retentate | 3.39% | 22.66% | 5.39% | 7.64% | 2.58% | 2.05 |
| Peak area | Permeate | 2.23% | 28.09% | 3.49% | 4.51% | 1.45% | 5.65 |
| Calculated | % Rejection | −18.06% | −3.22% | 9.41% | 8.67% | 11.87% | |
| | | PM2 Membrane #2 Product PM10 Permeate | | | | | |
| Peak area | Feed | 2.23% | 28.09% | 3.49% | 4.51% | 1.45% | 5.65 |
| Peak area | Retentate | 3.98% | 26.07% | 3.64% | 6.54% | 2.96% | 3.65 |
| Peak area | Permeate | 3.65% | 22.14% | 4.52% | 6.99% | 2.37% | 2.05 |

The observed % rejection can be influenced by the concentration in the feed as well as the molecular size. These results are understood to mean that all the components are permeable to the PM10 membrane, including much of the color. Subsequent fractionation of the PM10 permeate using the PM2 membrane enabled removal of the color bodies as in Example 1.

(c) providing at least one step of membrane fractionation to filter said crude plant extract after removal of said volatile components using a semi-permeable membrane having a porosity ranging between 2,000 to 10,000 nm wco, and
   (d) forming a permeate and a retentate, wherein the permeate is collected for about 2 hours by using a flow rate of 80 ml/min or the permeate is collected for about 3 hours by using a flow rate of 5.5 ml/min to 17 ml/min, wherein the permeate at the end of fractionation is characterized by having a higher total percentage of a mixture of rebaudioside A and stevioside in the permeate compared to total percentage of a mixture of rebaudiosides F, D, C and dulcoside A in the permeate.

2. The composition of claim 1, wherein the crude extract of *stevia* comprises a sweet-tasting terpenoid glycoside.

3. The composition of claim 1, wherein the crude extract of *stevia* comprises a natural high intensity sweetening compound that is an extract selected from the group consisting of *Stevia rebaudiana, Glycyrrhiza glabra, Siraitia grosvenorii* and mixtures thereof.

4. The composition of claim 3, wherein the natural high intensity sweetening compound is modified by enzymatic or microbial fermentation.

5. The composition of claim 1, further comprising flavor modifiers.

6. The composition of claim 1, wherein the sweetening composition is subjected to a drying process.

7. The composition of claim 1, wherein the sweetening composition is combined with a carrier material.

8. The composition of claim 7, wherein the sweetening composition is co-crystallized with the carrier material.

9. The composition of claim 7, wherein the sweetening composition has less than 0.25 kcal per gram of SES.

10. The composition of claim 7, wherein the sweetening composition has a density of from about 0.1 g/cm$^3$ to about 0.8 g/cm$^3$.

11. The composition of claim 7, wherein the sweetening composition has a ratio of carrier material to plant based natural high intensity sweetening compound of from about 1:1 to about 99:1.

12. The composition of claim 7, wherein the sweetening composition has a ratio of carrier material to plant based natural high intensity sweetening compound of from about 30:1 to about 40:1.

13. The composition of claim 7, wherein the composition is a powder or concentrate.

14. The composition of claim 7, further comprising a plant based natural low intensity sweetening compound.

15. The composition of claim 14, wherein the crude extract of *stevia* includes the plant based natural low intensity sweetening compound.

16. The composition of claim 14, wherein the plant based natural low intensity sweetening compound is a fruit-derived sweetener.

17. The composition of claim 1, wherein the process of making the composition does not include treatments with ion exchange resins, treatments with carbon based or resin based decoloring agents, or crystallization with carbon based solvents to remove volatile components.

* * * * *